(12) United States Patent
Vaillon et al.

(10) Patent No.: US 9,797,847 B2
(45) Date of Patent: Oct. 24, 2017

(54) DEVICE FOR NEAR FIELD AND FAR FIELD IMAGING IN THE MICROWAVE RANGE

(71) Applicants: INSTITUT NATIONAL DES SCIENCES APPLIQUEES DE LYON, Villeurbanne (FR); CENTRE NATIONAL DE LA RECHERCHE SCIENTIFIQUE (CNRS), Paris (FR); UNIVERSITE CLAUDE BERNARD LYON 1, Villeurbanne (FR); UNIVERSITE D'AIX MARSEILLE, Marseilles (FR)

(72) Inventors: Rodolphe Vaillon, Lyons (FR); Bernard Lacroix, Sainte Consorce (FR); Jean-Michel Geffrin, Plan de Cuques (FR); Mathieu Francoeur, Salt Lake City, UT (US)

(73) Assignees: Institut National Des Sciences Appliquees De Lyon, Villeurbanne (FR); Centre National De La Recherche Scientifique (CNRS), Paris (FR); Universite Claude Bernard Lyon 1, Villeurbanne (FR); Universite D'Aix Marseille, Marseilles (FR)

( * ) Notice: Subject to any disclaimer, the term of this patent is extended or adjusted under 35 U.S.C. 154(b) by 0 days.

(21) Appl. No.: 14/780,061

(22) PCT Filed: Mar. 28, 2014

(86) PCT No.: PCT/EP2014/056351
§ 371 (c)(1),
(2) Date: Sep. 25, 2015

(87) PCT Pub. No.: WO2014/154888
PCT Pub. Date: Oct. 2, 2014

(65) Prior Publication Data
US 2016/0054238 A1 Feb. 25, 2016

(30) Foreign Application Priority Data

Mar. 28, 2013 (FR) ...................................... 13 52803

(51) Int. Cl.
*G01R 27/32* (2006.01)
*G01S 13/00* (2006.01)
(Continued)

(52) U.S. Cl.
CPC ............. *G01N 22/00* (2013.01); *G01Q 60/22* (2013.01); *B82Y 20/00* (2013.01); *B82Y 35/00* (2013.01)

(58) Field of Classification Search
CPC ............................... G01N 22/00; G01Q 60/22
(Continued)

(56) References Cited

U.S. PATENT DOCUMENTS

2002/0105455 A1* 8/2002 Wright ...................... G01S 7/03
342/22
2004/0155665 A1* 8/2004 Arnone .............. G01N 21/3581
324/644
(Continued)

FOREIGN PATENT DOCUMENTS

CN 102590156 A 7/2012

OTHER PUBLICATIONS

Beruete, M., et al.; "Single negative birefringence in stacked spoof plasmon metasurfaces by prism experiment," Optics Letters, Optical Society of America, vol. 35, No. 5, Mar. 3, 2010, pp. 643-645.
(Continued)

*Primary Examiner* — Farhana Hoque
(74) *Attorney, Agent, or Firm* — Harness, Dickey & Pierce, PLC

(57) ABSTRACT

A device for the imaging of an object to be studied, combines: a prism made from a material with no losses
(Continued)

(non-absorbent) for radiation in the microwave range; a sample holder on a front face of the prism for receiving the object to be studied; and a mobile emitting antenna on a rear face of the prism in order to emit radiation in the microwave range.

16 Claims, 2 Drawing Sheets

(51) Int. Cl.
    *G01N 22/00*     (2006.01)
    *G01Q 60/22*     (2010.01)
    *B82Y 20/00*     (2011.01)
    *B82Y 35/00*     (2011.01)

(58) Field of Classification Search
    USPC .................................. 324/637, 642; 342/22
    See application file for complete search history.

(56) References Cited

U.S. PATENT DOCUMENTS

| | | | |
|---|---|---|---|
| 2008/0054894 A1* | 3/2008 | Sasaki | B82Y 25/00 324/252 |
| 2010/0109680 A1* | 5/2010 | Adams | G01R 27/04 324/642 |

OTHER PUBLICATIONS

Carney, P. Scott, et al.; "Computational Lens for the Near Field," Physical Review Letters, vol. 92, No. 16, Apr. 1, 2004, 4 pages.

Carney, P. Scott, et al.; "Near-Field Tomography," Inside Out: Inverse Problems, MSRI Publications, vol. 47, Jan. 1, 2003, pp. 131-166.

Culshaw, W., et al.; "Effect of a Metal Plate on Total Reflection," Proceedings of the Physical Society, Section B, vol. 66, No. 10, Jan. 1, 1953, pp. 859-864.

Francoeur, Mathieu, "Near-Field Radiative Transfer: Thermal Radiation, Thermophotovoltaic Power Generation and Optical Characterization," University of Kentucky Doctoral Dissertations, paper 58, Jan. 1, 2010, 52 pages.

Safarov, V.I., et al.; "Near-field magneto-optics with polarization sensitive STOM," Ultramicroscopy 57, Feb. 1, 1995, pp. 270-276.

Gaikovich, K. P., "Subsurface Near-Field Scanning Tomography," Physical Review Letters, vol. 98, No. 18, May 4, 2007, 4 pages.

Hibbins, A. P., et al.; "Prism coupling to 'designer' surface plasmons," Optics Express, vol. 16, No. 25, Dec. 8, 2008, pp. 20441-20447.

Lai, Brian C. H., et al.; "Surface Electromagnetic Wave Field Strength Measurements on Railroad Tracks," IEEE Transactions on Microwave Theory and Techniques, IEEE Service Center, vol. MTT-28, No. 8, Aug. 1, 1980, pp. 919-924.

Radiative Energy Transfer Lab Publications; URL: http://www.retl.utah.edu/index.php/Publications, Feb. 24, 2014, 6 pages.

Schoenlinner, B., et al.; "Compact Multibeam Imaging Antenna for Automotive Radars," IEEE MTT-S Digest, IF-WE-57, Jun. 2, 2002, pp. 1373-1376.

Short, Mitchell R., "The Discrete Dipole Approximation with Surface Interaction for Evanescent Wave-Based Characterization of Nanostructures on a Surface with Validation Against Experimental Results," A Thesis, Department of Mechanical Engineering, University of Utah, Mar. 12, 2013, 28 pages.

Vaillon, Rodolphe, et al.; "A new implementation of a microwave analog to light measurement device," Journal of Quantitative Spectroscopy & Radiative Transfer 112, Jul. 1, 2011, pp. 1753-1760.

\* cited by examiner

DEVICE FOR NEAR FIELD AND FAR FIELD IMAGING IN THE MICROWAVE RANGE

CROSS-REFERENCE TO RELATED APPLICATIONS

This application is a National Phase Entry of International Application Serial No. PCT/EP2014/056351 filed on Mar. 28, 2014, which claims priority to French Patent Application Serial No. 1352803, filed on Mar. 28, 2013, both of which are incorporated by reference herein.

BACKGROUND

The present invention relates to the general technical field of imaging devices allowing the study of samples, notably in the near field or in the far field.

The worldwide development of nanosciences and of nanotechnologies generates research efforts setting into play nanostructures of increasing complexity, in order to give them diverse and varied novel functionalities. This induces the requirement for developing novel characterization (size, structure, optical properties, thermal properties, etc.) and control devices and methods for nano-objects, such as nanoparticles for designing novel materials. Within the scope of the present description of the invention, by "nano-object" is meant a body for which at least one of the dimensions (length, diameter, thickness) is of the order of one nanometer, i.e. less than 100 nanometers and preferentially less than 50 nanometers.

The optical viewing devices—such as optical microscopes—remain attractive because of their flexibility. Such devices conventionally include:
- a source of light for illuminating an object to be studied,
- a detector for detecting the light emitted by the source.

However, these optical devices are presently limited in resolution, notably for viewing objects for which one of the dimensions is less than one half-wavelength of the light emitted by the source. Indeed, when an object has a dimension of less than one half-wavelength of the light which illuminates it, the light is scattered as a spot. It is therefore not possible to obtain a sharp image of the studied object. This fundamental limitation is due to the fact that detection and measurement of the electromagnetic field are achieved at a distance of the order of several wavelengths from the studied object.

Now, two regions in which are found electromagnetic fields of different natures have to be distinguished:
- the first region, located at a distance greater than several times the wavelength of the illumination light is said to be a "far field area"; the electromagnetic field which may be measured in the far field area is formed with so-called "propagative" waves,
- the second region which is confined in the vicinity of the surface of the studied object is a so-called "near field area"; the electromagnetic field which may be measured in the near field area is formed by the propagative waves mentioned earlier, associated with so-called "evanescent" waves which are too strongly attenuated for being detectable further away, in other words, the waves decrease exponentially with distance and are only detectable in the vicinity of the surface of the studied object.

In order to attempt to get over resolution limit, it is possible to resort to other excitation modes of the studied object in other ranges of frequencies (wavelengths).

An object of the present invention is to propose in the microwave range an imaging device similar to the one allowing characterization and control of an object, such as a nano-object, in optics. Such a device may also be advantageously utilized in microwaves for non-destructive evaluation of macro-objects consisting of various materials, either manufactured materials such as dielectrics or composites, or natural materials like wood.

SUMMARY

One of the objects of the invention is to propose an imaging device for which the quality is improved by controlling the evanescent wave which is generated. To do this, the invention proposes a combination of a source of waves and of an improved generator of evanescent waves in the wave range of microwaves, used as an excitation source for an imaging device allowing analysis of an object.

Most particularly, the invention proposes an imaging device for an object to be studied, which is remarkable in that the composition includes as a combination:
- a prism in a lossless (non-absorbent) material for electromagnetic waves in the microwave range,
- a sample holder on the planar face of the prism (or front face), for receiving the object to be studied,
- at least one emitting antenna on a rear face of the prism for emitting radiation in the range of microwaves, said and at least one emitting antenna being matched in impedance so as to directly radiate into the prism. The emitting antenna(s) are found in proximity to the surface of the semi-circular portion of the prism, for emitting radiation in the microwave range.

One of the advantages of the imaging device of the invention lies in the fact that by means of this impedance matching between the antenna and the prism, the quality of the device is substantially improved in order to have optimum transmitted energy, by controlling the evanescent wave which is generated. Indeed, in the invention, there is only the evanescent wave which leaves the prism, the transmitted wave is no longer propagative but becomes the evanescent wave which propagates parallel to the surface of the prism. The result of this is good control of the excitation with the device of the invention.

Advantageously, the emitting antenna(s) may extend inside the prism (it is or they are in this case "embedded" in the prism), or extend outside the prism. In every case, by "antenna found in proximity of the surface of the semicircular portion of the prism", is meant an antenna located at a distance of less than or equal to 15 centimeters from the surface of the prism. In the case of a nano-object observed via waves of visible or infrared light, the great difficulty in preparing perfectly controlled samples (deposition of nanoparticles on the surface, etc.), and the inexistence of any imaging device with sufficient resolution make the study difficult for this nano-object.

The solution according to the invention consists of applying a so-called "microwave analogy" principle, by carrying out a double change in scales (size [nanometer=>centimeter] and wavelength [visible=>microwaves]) by an identical factor. The problem is then strictly identical provided that the studied objects strictly have, in the translated range of microwaves, the same electromagnetic properties as those which are applied in visible light. The nano-objects are replaced with macro-objects for which manufacturing and positioning become much more feasible. Further, the amplitude and the phase of the fields are accessible through measurement, which allows evaluation of the electromagnetic models in primary variables.

Within the scope of the present invention, by "impedance-matched emitting antenna" is meant an emitting antenna for which the characteristic impedance in the material (of the prism) is close to that of the measurement apparatus. The result of this is that the wave emitted by the antenna does not undergo any loss at the antenna/prism interface and is entirely transmitted directly into the latter.

Preferred but non-limiting aspects of the method for transmitting data, described above, are the following:
- the imaging device includes a far field receiving antenna for sensing the electromagnetic radiation transmitted by the object to be studied,
- the imaging device further includes near field spatially localized measurement probes,
- said and at least one emitting antenna includes a mobile emitting antenna mounted on a mechanical system allowing displacement of the mobile emitting antenna along a displacement area,
- the emitting antenna includes a coupling material, for which the permittivity is substantially equal to the permittivity of the material making up the prism,
- said at least one emitting antenna includes a plurality of elementary antennas distributed in the vicinity of the rear face of the prism, said elementary antennas being supplied with electric current, sequentially, pairwise or simultaneously, so that said elementary antennas emit radiation sequentially, pairwise or simultaneously,
- this gives the possibility of doing without a mechanical system on which is mounted a mobile emitting antenna on the one hand and of producing a mixture of waves and thereby making an adaptive antenna for several waves on the other hand; however, one skilled in the art will appreciate that the device may include as a combination, a mobile emitting antenna connected to a mechanical system allowing displacement of the latter, and elementary antennas distributed in the vicinity of the rear face of the prism (typically at a distance from the surface of the semi-circular portion of the prism, of less than or equal to 10 centimeters); in this case, these emitting antennas may be activated sequentially or in parallel or pairwise, etc., so as to give the possibility of conducting various near or far field measurements;
- the coupling material is a mixture of air and of silica,
- the prism has a hemi-cylindrical shape,
- the prism includes a material layer absorbing radiations in the microwave range, said layer extending over all the surfaces of the prism except for the upper face and the displacement area of the emitting antenna;
- the prism includes a material layer absorbing radiations in the microwave range, said layer extending over all the surfaces of the prism other than the upper face and regions of the prism in vicinity to the elementary antennas;
- the sample holder includes positioning markers.

The invention also relates to the use of the device according to one of the preceding claims in an anechoic chamber.

BRIEF DESCRIPTION OF THE DRAWINGS

Other advantages and features of the device according to the invention will further become apparent from the description which follows of several alternative embodiments, given as non-limiting examples, from the appended drawings wherein.

DETAILED DESCRIPTION

Figure 1:
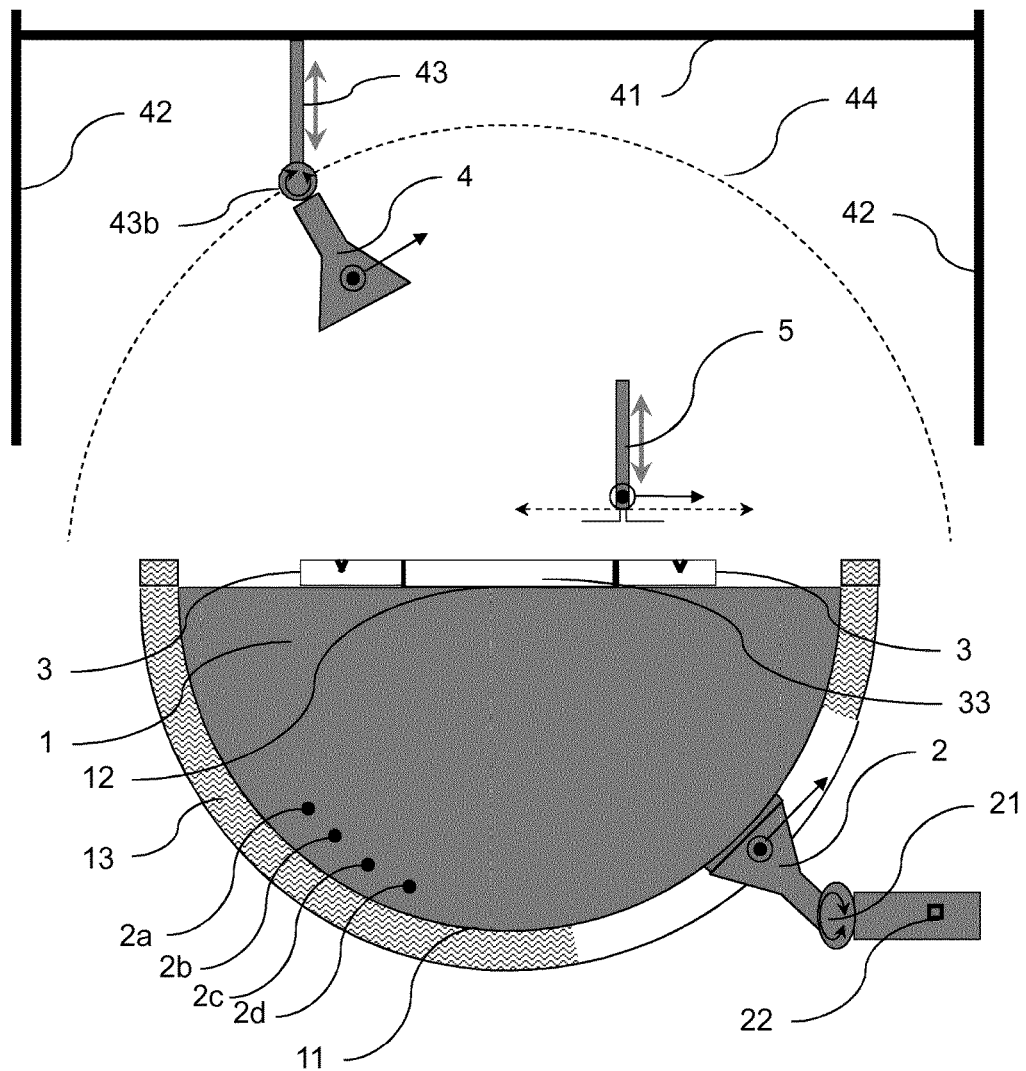
FIG. 1 illustrates an embodiment of an imaging device.
Figure 2:
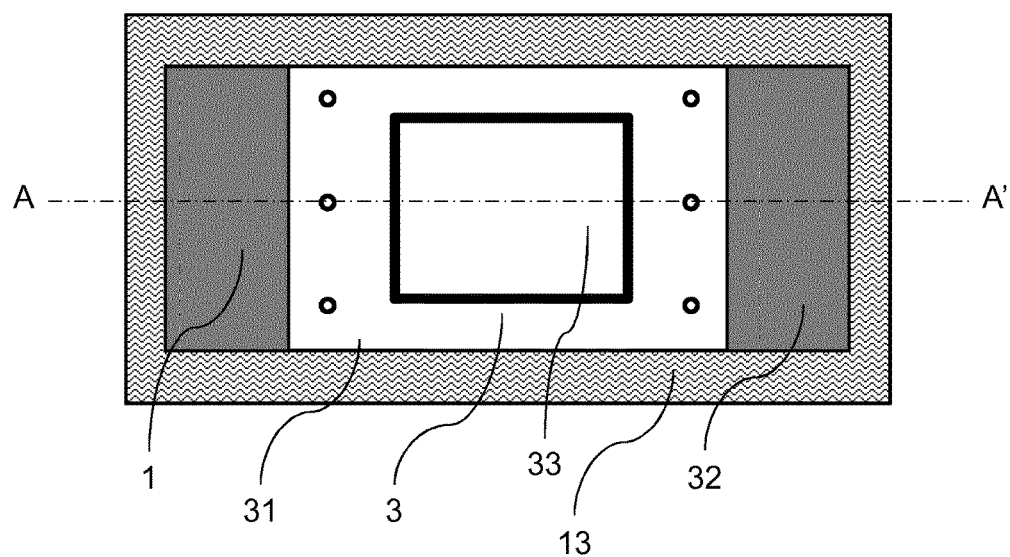
FIG. 2 is a top view of a prism provided with a sample holder.

An exemplary imaging device according to the invention will now be described. The device includes a prism 1, an emitting antenna 2, a sample holder 3 on the prism 1, a receiving antenna 4 and a receiving probe 5.

Prism

In the embodiment illustrated in FIG. 1, the prism 1 has a hemi-cylindrical shape. It includes a convex rear face 11, and a planar front face 12. The half-cylinder forming the prism 1 is for example with a diameter equal to sixty centimeters. Of course, the prism 1 may have other shapes such as a hemispherical shape.

The prism 1 gives the possibility of generating the evanescent waves emitted on its front face 12 by total internal reflection of the waves emitted by the emitting antenna 2 directly into the latter. In other words, the wave transmitted from the emitting antenna 2 is no longer propagative but becomes the evanescent wave which propagates parallel to the surface of the prism, in particular at the prism/sample holder separation interface and which interacts with the sample to be studied.

The prism 1 is in a material not having any losses for microwave radiations such as a polymer of the polyamide PA6 type. Advantageously, all the surfaces of the prism except for the upper surface and the displacement area of the emitting antenna may be covered with a material 13 absorbing microwave radiations. This allows a reduction in the influence of parasitic noises in the measurement of the electromagnetic waves propagated by the studied object.

Emitting Antenna

The emitting antenna 2 allows generation of radiation in the microwave range. More specifically, the wavelength of the radiation emitted by the emitting antenna 2 is typically comprised between 7.5 millimeters and 30 centimeters depending on the selection of the antenna 2 (frequency comprised between 1 GHz and 40 GHz). The emitting antenna 2 is positioned on the rear face 11 of the prism 1. In particular, the emitting antenna 2 may move on the convex face of the hemi-cylindrical prism. For example it is of the Horn type, and is in contact with the rear face 11 of the prism 1.

The emitting antenna 2 is mounted on a jointed arm 21. The jointed arm 21 allows displacement in translation and rotation of the emitting antenna 2 with respect to the prism 1. Preferably, the emitting antenna 2 may be mounted in several ways for generating polarized microwave radiation of type S or of type P or further elliptically polarized radiation.

The jointed arm 21 may include an angular sensor 22 for measuring the angle between the planar surface of the prism (the horizontal) 1 and the arm 2. This allows control of the angle of incidence of the radiation emitted by the emitting antenna 2, and thus control of the penetration depth of the surface wave generated in the air above the prism 1 from said radiation emitted by the emitting antenna 2.

The emitting antenna 2 includes a coupling material giving the possibility to the emitting antenna of emitting into a medium for which the permittivity is quasi identical (to within 5%) with that of the material forming the prism. This gives the possibility of avoiding reflection losses of the radiation at the interface between the antenna and the prism, thereby allowing improvement in the measurement quality of the device of the invention. Advantageously, the coupling material has the same physical properties as the material forming the prism in the microwave range. For example, the coupling material consists of a mixture of silica and air (i.e. sand).

Sample Holder

The sample holder 3 is intended to receive the object to be studied. It gives the possibility of ensuring accurate positioning of the studied object on the prism 1. The sample holder 3 is made in a material transparent to microwave radiation, such as polystyrene. It extends over the front face 12 of the prism 1.

The sample holder 3 may include an outer frame 31 attached to the prism 1. This outer frame 31 includes housings intended for receiving positioning markers 32 such as spheres. These spheres may be made in a material transparent to visible light such as Plexiglas. The number of spheres is preferably greater than or equal to three. These spheres are used as an alignment mark of the assembly consisting of the prism 1, of the emitting antenna 2 and of the studied object in a fixed reference system. The position of the spheres may be detected via a conventional detection system known to one skilled in the art and for example including a HeNe laser diode for illuminating the Plexiglas beads. This gives the possibility of accurately determining the position of the prism and of the studied object relatively to the antennas and to their positioning systems, which is notably important for measuring the phase of the electromagnetic fields generated by the object when the latter is irradiated by the emitting antenna.

The sample holder 3 may also include an inner frame 33 for which dimensions are provided for allowing its fitting into the outer frame 31. This inner frame 33 is used for supporting the studied object. The inner frame 33 may be machined with imprints corresponding to the studied object to be positioned on the plane of the prism.

Far Field Receiving Antenna

The receiving antenna 4 gives the possibility of measuring the amplitude and the phase of the electromagnetic waves scattered/channeled/diffracted by the object to be studied in a far field, and this for both polarization components of types S and P. The receiving antenna 4 is connected to a displacement system 41, 42, 43, 43b allowing:

its rotation relatively to the prism 1, and
its translation relatively to the prism 1.

The displacement system for example includes a horizontal rail 41 slidably mounted on two vertical rails 42 (or a vertical rail slidably mounted on two horizontal rails), a base 43 slidably mounted on the horizontal rail 41 (or on the vertical rail), the receiving antenna 4 being pivotally mounted on the base 43. This allows translational displacement of the receiving antenna 4 along two directions and its rotary displacement around a pivot connection between the base 43 and the receiving antenna 4.

The translational displacements of the receiving antenna 4 along two directions allow its positioning in space relatively to the prism 1. The rotary displacement 43b of the receiving antenna 4 allows the latter to be oriented towards the object to be studied. The displacement system 41, 42, 43, 43b thus allows the receiving antenna 4 to describe a circular arc trajectory 44 around the prism 1 on which rests the sample holder 3. It is thus possible to conduct far field radiation diagram measurements.

Near Field Measurement Probe

The measurement probe 5 gives the possibility of measuring an electromagnetic wave in a near field. In particular, it allows detection of the evanescent waves generated by the surface of the sample to be studied and which have interacted with the latter. This measurement probe 5 may be of different types, whether in its principle (perturbing probe or not), its composition (metal, dielectric, etc.) or its polarization (electric monopole, dipole, magnetic loop, etc.).

The measurement probe 5 may be associated with specific displacement means or associated with the displacement system 41, 42, 43 of the receiving antenna 4. In this case, the receiving antenna 4 is replaced with the measurement probe 5 in order to conduct near field measurements. The displacement system 41, 42, 43 then allows positioning of the receiving antenna in proximity to the sample holder 3.

Operating Principle

The operating principle of the imaging device described above is the following. In a near field, the object to be studied is deposited with the sample holder 3. The measurement probe 5 is moved to the selected distance of the object by means of the displacement system 41, 42, 43. Measurement of the transmission of the electromagnetic wave between the emitting antenna and the measurement probe is then applied (with a network analyzer typically) for different positions of the measurement probe.

In a far field, the measurement probe 5 is replaced with the receiving antenna 4. The latter is moved to the intended distance from the object on a circular arc 44, on a line or on a plane (the geometry of which is conditioned by the positioners). The measurement is repeated with and without the object in order to extract the sole contribution of the object (diffracted field) by complex subtraction of both measured fields. It should be noted that the measurement probe 5 or the receiving antenna 4 are positioned on the side of the face on which the evanescent wave is generated and not on waves reflected by the emitting antenna 2/prism interface.

Advantageously, the imaging device described above may be positioned in an anechoic chamber. An advantage of such a chamber is that it consists of walls absorbing electromagnetic waves so that the latter propagate without any reflection. This gives the possibility of limiting the risks of perturbation of the measurements conducted on the object by reflection of the electromagnetic waves on the walls of the chamber.

The near field or far field imaging "microwave" device described above opens up many perspectives which will contribute to applying evanescent waves in future high resolution imaging systems. As the use of microwaves make the various constitutive elements and the measurement tools much more easy to handle, this device should allow better control and understanding of the phenomena set into play. It will also contribute to validating models describing complex phenomena like: coupling by mode hybridization, Fano resonances, structuration of evanescent waves or measurement of the local density of photon states (LDOS) in proximity to nanostructures.

The reader will have understood that many modifications may be made to the device described above without materially departing from the novel teachings and advantages described here. For example, the mobile emitting antenna attached to the displacement system 41, 42, 43 may be replaced with a plurality of elementary antennas 2a, 2b, 2c, 2d. This gives the possibility of doing without the presence of the displacement system.

In this case, the elementary antennas are positioned in a plurality of positions in vicinity to the rear face 11 of the prism. They may extend either outside the prism, or inside the prism (i.e. embedded in the prism). Within the scope of the present invention by "vicinity of the rear face of the prism" is meant a distance comprised between 0 and 15 cm between the rear face of the prism and the elementary emitting antenna. For example, each emitting antenna may be integrated to the prism, and extend at a distance of 10 cm from the rear face of the prism. Further for example, each antenna may be distant from the prism and extend at a distance of 15 cm from the rear face of the prism.

Of course, the imaging device may also include as a combination, a mobile emitting antenna attached to the displacement system 41 and a plurality of emitting antennas 2$a$, 2$b$, 2$c$, 2$d$ located in the vicinity of the rear face of the prism.

In the case when the imaging device includes a plurality of elementary emitting antennas positioned inside the prism, a radiation-absorbing material in the microwave range may be positioned on all the surfaces of the prism other than the front face as well as outlet locations of electric power supply cables of the elementary emitting antennas. When the emitting antennas are positioned outside the prism, the absorbing material may be positioned on all the surfaces of the prism other than the front face and the regions of the prism facing the elementary antennas.

Therefore, all the modifications of this type are intended to be incorporated within the scope of the appended claims.

The invention claimed is:

1. A device for imaging an object to be studied, wherein the device comprises:
   a prism in a lossless material for radiations in a microwave range;
   a sample holder on a front face of the prism, for receiving the object to be studied; and at least one emitting antenna on a rear face of the prism for emitting the radiation in the microwave range, the at least one emitting antenna being impedance-matched for directly radiating into the prism; wherein the prism is configured to perform total internal reflection of waves emitted by the at least one emitting antenna directly into the prism to generate evanescent waves emitted from the front face of the prism.

2. The emitting device according to claim 1, further comprising a far field receiving antenna for sensing the electromagnetic radiation transmitted by the object to be studied for polarization components of type S and type P.

3. The imaging device according to claim 1, further comprising a near field spatially localized measurement probe.

4. The imaging device according to claim 3, wherein the measurement probe measures an electromagnetic wave in the near field.

5. The imaging device according to claim 3, wherein the measurement probe measures evanescent waves generated by a surface of the object to be studied.

6. The imaging device according to claim 1, wherein the at least one emitting antenna includes a mobile emitting antenna mounted on a mechanical system allowing displacement of the mobile emitting antenna along a displacement area.

7. The imaging device according to claim 6, wherein the prism includes a material layer absorbing radiations in the microwave range, the layer extending over all the surfaces of the prism other than the upper face and the displacement area.

8. The imaging device according to claim 1, wherein the at least one emitting antenna includes a plurality of elementary antennas distributed in the vicinity of the rear face of the prism, the elementary antennas being supplied with electric current sequentially, pairwise or simultaneously, so that the elementary antennas emit radiation sequentially, pairwise or simultaneously.

9. The imaging device according to claim 8, wherein the prism includes a material layer absorbing the radiations in the microwave range, the layer extending over all the surfaces of the prism other than the upper face and regions of the prism in the vicinity of the elementary antennas.

10. The imaging device according to claim 8, wherein the prism includes a material layer absorbing radiations in the microwave range, the layer extending over all the surfaces of the prism other than the upper face.

11. The imaging device according to claim 1, wherein the emitting antenna includes a coupling material, the permittivity of which is substantially equal to the permittivity of the material making up the prism.

12. The imaging device according to claim 11, wherein the coupling material is a mixture of air and of silica.

13. The imaging device according to claim 1, wherein the prism is of a hemi-cylindrical shape.

14. The imaging device according to claim 1, wherein the sample holder includes positioning markers.

15. The use of the device according to claim 1 in an anechoic chamber or box.

16. A device for imaging an object to be studied, wherein the device comprises:
   a prism in a lossless material for radiations in a microwave range;
   a sample holder on a front face of the prism, for receiving the object to be studied; and
   at least one emitting antenna on a rear face of the prism for emitting the radiation in the microwave range, the at least one emitting antenna being impedance-matched for directly radiating into the prism; wherein the prism is of a hemi-cylindrical shape; wherein the prism transmits an evanescent wave out of the front face using total internal reflection of waves emitted by the at least one emitting antenna.

* * * * *